United States Patent [19]

Bowing et al.

[11] 4,051,059

[45] Sept. 27, 1977

[54] PEROXY-CONTAINING MICROBICIDES STABLE IN STORAGE

[75] Inventors: Walter Grosse Bowing; Hinrich Mrozek, both of Dusseldorf; Hans-Joachim Schlüssler, Haan; Bernd Tinnefeld, Velbert; Peter Vögele, Sindelfingen, all of Germany

[73] Assignee: Henkel & Cie GmbH, Dusseldorf-Holthausen, Germany

[21] Appl. No.: 711,206

[22] Filed: Aug. 3, 1976

[30] Foreign Application Priority Data

Aug. 16, 1975 Germany .............................. 2536617
Apr. 12, 1976 Germany .............................. 2616049

[51] Int. Cl.² ..................... A61K 33/40; A61K 7/135; C11D 7/18; C11D 7/38
[52] U.S. Cl. ...................................... 252/186; 252/95; 260/610 A; 423/272; 424/130
[58] Field of Search ................ 252/186, 95; 424/130, 424/62; 260/610 A; 423/272, 273

[56] References Cited

U.S. PATENT DOCUMENTS

| 3,684,477 | 8/1972 | Blumbergs et al. .................. 424/130 |
| 3,864,271 | 2/1975 | Stalter ................................. 252/186 |
| 3,907,991 | 9/1975 | Accetta ............................... 424/130 |

*Primary Examiner*—Benjamin R. Padgett
*Assistant Examiner*—Irwin Gluck
*Attorney, Agent, or Firm*—Hammond & Littell

[57] ABSTRACT

Peroxy-containing concentrates, stable in storage, useful for the production of functional agents consisting essentially of 0.5% to 20% by weight of peracetic or perpropionic acid or their precursors, 25% to 40% by weight of $H_2O_2$ 0 to 5% by weight of anionic surface-active compounds of the sulfonate and sulfate type, Remainder: water.

7 Claims, No Drawings

PEROXY-CONTAINING MICROBICIDES STABLE IN STORAGE

RELATED ART

It is known that the solutions of peracetic acid and perpropionic acid are functional agents which can be used for various purposes. They are suitable, for example, for the oxidation or organic material in general, as well as for the treatment of hair, straw and textiles. In particular, however, they can be used as microbicides and virucides. Peracetic acid is preferably employed in this connection.

The pure peracetic acids are problematic not only with regard to their preparation, but they are also difficult to handle because they are a fire and explosion hazard. For this reason the per acids are not used in practice in pure form but in mixtures of 35% to 45% peracetic acid and 40% to 55% acetic acid, for example. The amount of water present is generally below 15%. The disadvantage of these concentrates is that, due to their pungent odor and their corrosive effect, they can only be handled by the user under strict safety measures. The concentrates must be diluted first. If the concentrates are produced, for example, from 5% to 25% by weight of per acid alone and the balance water, these are not stable in storage.

OBJECTS OF THE INVENTION

An object of the present invention is the development of a peroxy-containing concentrate, stable in storage and useful for the production of functional agents, which is safe to handle and not unduly corrosive to human skin.

Another object of the present invention is the development of a peroxy-containing concentrate, stable in storage, consisting essentially of 1. from 0.5% to 20% by weight of an acid selected from the group consisting of peracetic acid, acetic acid, perpropionic acid, propionic acid, mixtures of peracetic acid and acetic acid, and mixtures of perpropionic acid and propionic acid,
2. from 25% to 40% by weight of $H_2O_2$,
3. from 0 to 5% by weight of an anionic surface-active compound selected from the group consisting of sulfonates and sulfates, and
4. the remainder to 100% by weight, water.

These and other objects of the invention will become more apparent as the description thereof proceeds.

DESCRIPTION OF THE INVENTION

It was now found that the above objects can be achieved and the disadvantages recited above can be avoided, and peroxy-containing concentrates which are stable in storage can be obtained which are useful for the production and supplementation of microbicides based in aliphatic monopercarboxylic acids. These peroxy-containing concentrates are characterized by a content of 0.5% to 20% by weight of a per acid with 2 to 3 carbon atoms and/or the corresponding aliphatic noncarboxylic acid, as well as 25% to 40% by weight of $H_2O_2$, and the balance, water.

More particularly, the invention relates to a peroxy-containing concentrate, stable in storage, consisting essentially of 1. from 0.5% to 20% by weight of an acid selected from the group consisting of peracetic acid, acetic acid, perpropionic acid, propionic acid, mixtures of peracetic acid and acetic acid, and mixtures of perpropionic acid and propionic acid,
2. from 25% to 40% by weight of $H_2O_2$,
3. from 0 to 5% by weight of an anionic surface-active compound selected from the group consisting of sulfonates and sulfates, and
4. the remainder to 100% by weight, water.

Preferably, the storage-stable peroxy-containing concentrates contain from 5% to 10% by weight of component (1), and a molar excess of $H_2O_2$ with reference to the acid component (1), calculated as the monocarboxylic acid, in a molar ratio of at least 2:1, preferably 3:1 to 50:1. When the anionic surface-active compound of the sulfonate and the sulfate type is present, it is preferably in an amount of from 0.5% to 5% by weight.

The production is effected in a simple manner by mixing an $H_2O_2$ solution, preferably with a concentration of about 33% by the weight with per acid such as peracetic acid and, optionally, acetic acid. The mixtures can also be produced in an advantageous manner by adding the corresponding amount of the acid, such as acetic acid, to the concentrated $H_2O_2$ solution. Since the products mainly are not used at once, but are first stored, a corresponding content of peracetic acid is formed when acetic acid is employed. The formation of peracetic acid can be catalytically accelerated, if desired, by adding a small amount of a mineral acid (0.1% to 1% by weight). In general, however, such an addition is not necessary for the above-mentioned reasons.

Such concentrates, which are produced, for example, from 30% of $H_2O_2$, 5% of acetic acid and 65% of water, have no annoying odor and are easy to handle, that is, they can be easily diluted to the concentration of 0.1% to 1%, as they are used in food technology and in the medical field, without requiring special precautions.

In view of the many possible uses of the above-described peroxy-containing concentrates as functional agents, for example, for the oxidation of organic material in general, or for the treatment of hair, straw and textiles, as well as the preparation of microbicides and virucides, it is sometimes of advantage to add a wetting agent in order to improve the desired properties further.

It was found that stable concentrates of the above-described type can be obtained if anionic surface-active compounds of the sulfonate and sulfate type, such as alkylbenzene sulfonates having 6 to 18 carbon atoms in the alkyl, alkyl sulfates and/or alkane sulfonates (each having 8 to 22 carbon atoms in the alkyl or alkane groups) are added in amounts of 0.05% to 5% by weight.

The alkylbenzene sulfonates which can be employed are preferably those which contain an alkyl radical of 6 to 18 carbon atoms, preferably 9 to 15 carbon atoms. Instead of the alkylbenzene sulfonates, alkyl sulfates or alkane sulfonates with an alkyl or alkane radical of the chain length 12 to 18 carbon atoms, can be employed. If desired, mixtures of the above-mentioned anionic surface-active compounds can naturally also be used.

It was found that, with the above-mentioned additives, the concentrates remain stable over long periods of time and that the content of peracetic acid in the concentrate thus also remains constant. However, if soaps or the conventional nonionic surface-active compounds are employed as the surface-active additive, a sufficient stability is not achieved.

The new stable peroxy-containing concentrates are useful in the production of functional agents which can be used for all purposes where an oxidizing effect is to be achieved and the disadvantages of the known pure per acids render their application difficult or impossible. The concentrates have, furthermore, the advantage that they can be employed to produce function agents for static disinfections to prevent the growth of germs on machines after cleaning, particularly in the food industry. Due to their content of $H_2O_2$, they have a long-term effect on most microorganisms.

The pH-value of the solution produced is still weakly acid, and the residues of acetic acid after the disinfection are extremely small, so that the agents are also suitable for disinfections where rinsing is no longer necessary.

The following examples are illustrative of the invention without being limitative in any respect.

EXAMPLE 1

A concentrate for the production of microbicides was prepared by mixing

5% by weight acetic acid
30% by weight $H_2O_2$
65% by weight water

The concentrate was allowed to stand and a sample was taken at intervals to determine the content of $H_2O_2$ and peracetic acid. The results are compiled in Table I. For comparison, another concentrate was prepared which contained 8% by weight of peracetic acid, 8.5% by weight of acetic acid, 1% by weight of $H_2O_2$ and 82.5% by weight of water. Samples were taken from this mixture at intervals and the content of peracetic acid was determined. The results are compiled in Table II. It can be seen clearly that the comparison agent was not stable.

TABLE I

| Time | $H_2O_2$ % | Peracetic acid % |
|---|---|---|
| 1 week | 28.5 | 3.3 |
| 1 month | 28.3 | 3.5 |
| 3 months | 28.3 | 3.5 |
| 6 months | 28.2 | 3.5 |

TABLE II

| Time | % by Weight Peracetic Acid |
|---|---|
| 1 hour | 7.6 |
| 10 hours | 6.1 |
| 2 days | 3.0 |
| 14 days | 1.2 |
| 1 month | 0.6 |

EXAMPLE 2

Concentrates of the composition indicated below (products A to C) were prepared from $H_2O_2$, acetic acid and water. These concentrates were left for about a week and then diluted to a 0.05% or 0.2% solution. Then the killing times were determined by means of the suspension test according to the guidelines of "Deutsche Gesellschaft for Hygiene und Mikrobiologie" (DGHM). Staphylococcus aureus and Escheria-coli were employed as test microorganisms. The values (killing times in minutes) are given in Table III below.

| Products | (Data in % by Weight) | | |
|---|---|---|---|
| | A | B | C |
| $H_2O_2$ | 23.1 | 23.1 | 23.1 |
| Acetic acid | 20 | 10 | 5 |
| $H_2O$ | 56.9 | 66.9 | 71.9 |

TABLE III

| Product | S. aureus | | | | | | E. coli | | | | | |
|---|---|---|---|---|---|---|---|---|---|---|---|---|
| | A | | B | | C | | A | | B | | C | |
| Concentration | 0.05% | 0.2% | 0.05% | 0.2% | 0.05% | 0.2% | 0.05% | 0.2% | 0.05% | 0.2% | 0.05% | 0.2% |
| Days | Killing time in minutes | | | | | | Killing time in minutes | | | | | |
| 10 | 5 | 1 | 5 | 2.5 | 10 | 5 | 5 | 1 | 30 | 2.5 | 40 | 2.5 |
| 60 | 5 | 1 | 5 | 2.5 | 10 | 5 | 5 | 1 | 30 | 2.5 | 40 | 2.5 |
| 90 | 5 | 1 | 5 | 2.5 | 10 | 5 | 5 | 1 | 30 | 2.5 | 40 | 2.5 |

EXAMPLE 3

Following the procedures of Example 2 and by using the suspension test according to the guidelines of DGHM, the killing times of Staphylococcus aureus was determined by means of mixtures of $H_2O_2$ and small amounts of acetic acid or propionic acid. The results are compiled in Table IV below.

TABLE IV

| ppm $H_2O_2$ | 1165 | 1165 | 1165 |
|---|---|---|---|
| ppm acetic acid | | 50 | |
| ppm propionic acid | | | 50 |
| Killing time (min.) | 20 | 5 | 5 |

EXAMPLE 4

A concentrate was prepared by mixing

5% by weight acetic acid
27.6% by weight $H_2O_2$
1% by weight alkyl-(C12-C18)-sulfonate as well as
66.4% by weight water The concentrate was allowed to stand at 20° C and a sample was taken at intervals to determine the content of $H_2O_2$ and peracetic acid. The results are compiled in Table V below.

TABLE V

Stability of the mixtures with addition of an alkyl sulfonate at 20° C.

| Time | % $H_2O_2$ | % Peracetic acid |
|---|---|---|
| Initial value | 26.2 | 2.3 |
| 1 month | 26.1 | 2.3 |
| 3 months | 25.1 | 2.3 |
| 6 months | 25.0 | 2.3 |

Practically the same results are obtained if the concentrate contained 1% of an alkyl sulfate (alkyl radical C12-C18), instead of the 1% of alkyl sulfonate.

EXAMPLE 5

In order to check the fungicidal and sporicidal action, concentrates were prepared with various wetting agent contents by mixing 5% by weight acetic acid
27.6% by weight $H_2O_2$
1 or 1.5% by weight dodecylbenzene sulfonate, as well as
66.4% or 65.9% by weight water.

The concentrates were allowed to stand for about a week and then diluted to a concentration of 1% and 2% respectively. The fungicidal and sporicidal action was determined in the suspension test according to the guidelines of "Deutsche Gesellschaft for Hygiene and Mikrobiologie" (DGHM) at 20° C.

The results (killing time in minutes) are compiled in Table VI below.

TABLE VI

Fungicidal and sporicidal action of the concentrate with different wetting agent contents

| Concentrate + % alkyl benzene- sulfonate (50%) | Concentration (%) of solution used | 1 | 2 | 3 |
|---|---|---|---|---|
| | | (killing time in minutes) | | |
| Without wetting agent | 1.0 | >60 | 40 | 5 |
| | 2.0 | >60 | 20 | 2.5 |
| 2.0 | 1.0 | 40 | 5 | 1 |
| | 2.0 | 20 | 2.5 | 1 |
| 3.0 | 1.0 | 40 | 5 | 1 |
| | 2.0 | 20 | 1 | 1 |

1 - *Aspergillus niger*
2 - *Per. camerunense*
3 - *Candida albicans*

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A peroxy-containing concentrate, stable in storage, consisting essentially of
   1. from 0.5% to 20% by weight of an acid selected from the group consisting of peracetic acid, acetic acid, perpropionic acid, propionic acid, mixtures of peracetic acid and acetic acid, and mixtures of perpropionic acid and propionic acid,
   2. from 25% to 40% by weight of $H_2O_2$,
   3. from 0 to 5% by weight of an anionic surface-active compound selected from the group consisting of sulfonates and sulfates, and
   4. the remainder to 100% by weight, water.

2. The peroxy-containing concentrate of claim 1 wherein component (1) is present in an amount of from 5% to 10% by weight, and said $H_2O_2$ of component (2) is present in a molar excess with reference to said acid of component (1), calculated as the monocarboxylic acid of a molar ratio of at least 2:1.

3. The peroxy-containing concentrate of claim 2 wherein said molar ratio of $H_2O_2$ to monocarboxylic acid is from 3:1 to 50:1.

4. The peroxy-containing concentrate of claim 3 wherein said component (3) is present in an amount of from 0.5% to 5% by weight.

5. The peroxy-containing concentrate of claim 4 wherein said anionic surface-active compound is selected from the group consisting of alkylbenzene sulfonates having from 6 to 18 carbon atoms in the alkyl, alkane sulfonates having from 8 to 22 carbon atoms in the alkane, and alkyl sulfates having from 8 to 22 carbon atoms in the alkyl.

6. The peroxy-containing concentrate of claim 1 wherein said component (3) is present in an amount of from 0.5% to 5% by weight.

7. The peroxy-containing concentrate of claim 6 wherein said anionic surface-active compound is selected from the group consisting of alkylbenzene sulfonates having from 6 to 18 carbon atoms in the alkyl, alkane sulfonates having from 8 to 22 carbon atoms in the alkane, and alkyl sulfates having from 8 to 22 carbon atoms in the alkyl.

* * * * *